United States Patent
Inzé et al.

(10) Patent No.: US 11,213,815 B2
(45) Date of Patent: Jan. 4, 2022

(54) NETWELL ASSAY PLATE SYSTEM (71) Applicants: VIB VZW, Ghent (BE); UNIVERSITEIT GENT, Ghent (BE)

(72) Inventors: Dirk Gustaaf Inzé, Moorsel-Aalst (BE); Stijn Dhondt, Balegem (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 384 days.

(21) Appl. No.: 16/325,838

(22) PCT Filed: Aug. 17, 2017

(86) PCT No.: PCT/EP2017/070874
§ 371 (c)(1),
(2) Date: Feb. 15, 2019

(87) PCT Pub. No.: WO2018/033603
PCT Pub. Date: Feb. 22, 2018

(65) Prior Publication Data
US 2019/0184392 A1    Jun. 20, 2019

(30) Foreign Application Priority Data
Aug. 18, 2016  (GB) .................................. 1614116

(51) Int. Cl.
*B01L 3/00*    (2006.01)
*B01L 9/00*    (2006.01)
*C12Q 1/02*    (2006.01)

(52) U.S. Cl.
CPC ......... *B01L 3/50255* (2013.01); *B01L 3/5085* (2013.01); *B01L 9/523* (2013.01); *C12Q 1/02* (2013.01); *B01L 2200/0642* (2013.01); *B01L 2200/0647* (2013.01); *B01L 2300/0618* (2013.01); *B01L 2300/0681* (2013.01); *B01L 2300/0829* (2013.01); *B01L 2300/0851* (2013.01); *B01L 2300/123* (2013.01); *B01L 2300/16* (2013.01); *B01L 2300/168* (2013.01)

(58) Field of Classification Search
None
See application file for complete search history.

(56) References Cited

U.S. PATENT DOCUMENTS

| | | | |
|---|---|---|---|
| 5,801,055 | A | 9/1998 | Henderson |
| 5,837,198 | A | 11/1998 | Itani |
| 5,972,694 | A | 10/1999 | Mathus |
| 7,135,148 | B2 | 11/2006 | DeSilets et al. |
| 7,968,061 | B2 | 6/2011 | Goodwin |
| 8,178,058 | B2 | 5/2012 | Park |

(Continued)

FOREIGN PATENT DOCUMENTS

| WO | 9919067 A1 | 4/1999 |
|---|---|---|
| WO | 2014064542 A2 | 5/2014 |

OTHER PUBLICATIONS

PCT International Search Report and Written Opinion, Application No. PCT/EP2017/070874, dated Nov. 6, 2017, 12 pages.

(Continued)

*Primary Examiner* — Robert J Yamasaki
(74) *Attorney, Agent, or Firm* — Patent Law Works, LLP (57) ABSTRACT

The invention relates to a device and a method for growing and screening of plant samples, comprising a specialized multiwell plate system well-suited for housing granular media, for use in in vivo screening methods of uninterrupted plant tissue growth.

15 Claims, 8 Drawing Sheets (56) References Cited

U.S. PATENT DOCUMENTS

| | | |
|---|---|---|
| 2002/0189374 A1 | 12/2002 | DeSilets et al. |
| 2003/0026738 A1 | 2/2003 | Everett |
| 2004/0087005 A1 | 5/2004 | Henderson et al. |
| 2005/0136506 A1 | 6/2005 | Kamath |
| 2006/0286003 A1 | 12/2006 | Desilets et al. |
| 2008/0096272 A1 | 4/2008 | Everett |
| 2013/0210131 A1 | 8/2013 | Renken |
| 2014/0273070 A1 | 9/2014 | Hale |

OTHER PUBLICATIONS

GB Intellectual Property Office Search Report, Application No. GB1614116.0, dated Dec. 22, 2016, 6 pages.
Millipore, Multiwell Solutions for Discovery Research and Sample Prep. Fisher Scientific, Multiwell Product Guide, 2008 www.millipore.com/multiscreen, 44 pages.
Pelco Prep-Eze, Rectangular Wellplate Inserts—Instructions, Technical Notes, Ted Pella. Inc., https://www.tedpella.com/technote_html/36168_36170_36172.pdf, Accessed 2019. 2 pages.

Figure 8 to granular media, such as soil, will result in unstable conditions, desiccation, and distortion of the sample, and inhomogeneous supply of the solution. In addition, these in vitro systems do not allow to irrigate solid supports in large enough volumes or do not provide the appropriate conditions, such as protection from light or suitable handling features. In vitro compound screening assay setups mostly fully drown the plant tissue samples into the liquid medium, and often result in oxygen deprivation and false positive results, thereby requiring additional selection testing in vivo, which remains a burden as it is laborious and time-consuming. In addition, the in vitro plate systems currently available are not suited for the use of solid granular media, such as soil, to allow immediate in vivo screening of plant samples, because nutrients or treatment solutions cannot be supplied to the granular media in a reproducible manner, leading to unreliable data.
NETWELL ASSAY PLATE SYSTEM

FIELD OF THE INVENTION

The invention relates to a device and a method for growing and screening of plant samples, comprising a specialized multiwell plate system well-suited for housing granular media, for use in in vivo screening methods of uninterrupted plant tissue growth.

BACKGROUND OF THE INVENTION

Screening assays are typically performed in multiple well plates, depending on the size of the screen or the type of the sample, with a number ranging from 6 to 384, or more, wells per plate, with the aim to identify new compounds, peptides, biologics, or in fundamental research to unravel new mechanisms of for instance plant growth and development. High-throughput screening requires a fast and reproducible system to allow a parallel processing of batches of samples, possibly using an automated robotics-controlled handling system. Although used effectively for the screening of liquid samples, the current multiple well plates are generally not suited or ineffective for screening plant and other tissues that require, or prefer, more complex environments such as solid support structures. Currently, the vast majority of plant tissue screening assays is performed in vitro in multiwell plate systems, by suspending the plant tissue in a liquid media within each well. However, the plant tissue is deprived of oxygen when sitting in the liquid, effectively "drowning" the plant tissue in an anaerobic environment. Other attempts using media avoiding drowning the plant tissue are applying more solid substrate on which the plant tissue may be supported above the fluid, such as a gel or filter paper disk, but experience difficulties to exchange and replenish solutions when the nutrients or media have been depleted. Another approach to aspirating and removing media and tissue byproducts is to use an assay plate having a plurality of wells, with each well having a hole or port at the base of the well. A filter is positioned at the bottom of each well to support the tissue. Spent media can be vacuum harvested from each well through the port using a vacuum manifold assembly. One example of a vacuum manifold assembly is the MultiScreen$_{HTS}$ Vacuum Manifold system manufactured by MILLIPORE (Merck).

Although the filter disks in the assay plate allow media to be drawn out of the plate, it is difficult for the filter disks to retain enough media to support tissue maintenance and growth for any length of time. Another system provided by MILLIPORE is the Millicell multiwell cell culture plates (U.S. Pat. No. 7,018,588B2), providing an access port besides each well to allow media exchange without sample disturbance. This system allows in vitro use for cell culture and imaging of the samples without any movement, by using transparent plates. However, the system is only providing a test environment for liquid media, and does not allow fast and homogenous medium exchange or nutrient addition for solid supports, which is the case for all known available systems.

So in conclusion, the problem is that the use of such in vitro multiwell plate systems for the purpose of in vivo screening assays of uninterrupted plant tissue growth, which requires periodic homogenous addition of nutrition solutions to granular media, such as soil, will result in unstable conditions, desiccation, and distortion of the sample, and inhomogeneous supply of the solution. In addition, these in vitro systems do not allow to irrigate solid supports in large enough volumes or do not provide the appropriate conditions, such as protection from light or suitable handling features. In vitro compound screening assay setups mostly fully drown the plant tissue samples into the liquid medium, and often result in oxygen deprivation and false positive results, thereby requiring additional selection testing in vivo, which remains a burden as it is laborious and time-consuming. In addition, the in vitro plate systems currently available are not suited for the use of solid granular media, such as soil, to allow immediate in vivo screening of plant samples, because nutrients or treatment solutions cannot be supplied to the granular media in a reproducible manner, leading to unreliable data.

Accordingly, it would be advantageous to have a multiwell plate system and method in place for direct in vivo high-throughput compound screenings of uninterrupted plant tissue growth in, for instance, soil, thereby circumventing in vitro selection assays. In vivo screening systems using a multiwell plate system in which plant tissue is allowed to be grown in natural substrate (such as soil), in suitable conditions (i.e. roots protected from light, stable humidity), and which allow automated watering/compound addition without disturbance of the sample would also be an advantage. In addition, it would be advantageous that such a multiwell plate system allows to perform high-throughput screening assays, i.e. ensuring homogenous distribution of the solution in large enough volumes while retaining the soil in the well-compartment, for stable humidity conditions, to obtain reproducible results. Furthermore, it would be helpful for optimal setup of screening assays when each sample can be treated individually, since this would allow to test the most versatile combinations within the same assay conditions, and would avoid contamination issues between different samples of the same plate. Finally, another advantage of such a system would be that compounds are applied via the support medium, such as soil, and spraying is not required.

SUMMARY OF THE INVENTION

The present invention relates to a multiwell plate system and a method to grow and screen for plant samples supported by a granular medium, such as soil, thereby for the first time allowing high-throughput in vivo screening assays without need for a preceding in vitro selection, in suitable conditions for uninterrupted plant growth.

In a first aspect, the multiwell plate system comprises a netwell insert plate and an irrigation plate, to be mounted onto each other, and is further characterized in that said netwell insert plate comprises a multiplicity of well openings and access holes, characterized in that said access holes are equal in number to said well openings, and each one of said access holes being positioned besides such a well opening, i.e. the access hole is separated from its adjacent well opening by the plate body. Said netwell insert plate further comprises a hollow chamber connected to and extending downwards from the well opening, to be mounted in the irrigation plate its corresponding well. Said hollow chamber is sealed in the bottom with a porous membrane, wherein said porous membrane has a pore size of 200 μm to 1000 μm, allowing to house granular media inside said hollow chambers as sample support, and allowing to robustly irrigate said granular media. Said netwell insert plate further comprises an irrigation channel extending inwardly in connection with said access holes, wherein said access hole is separated from the adjacent well openings by the plate body in the insert netwell plate, and wherein said irrigation channel has an open end to allow passing through of solutions added via the access holes to the corresponding wells of the irrigation plate, thereby providing a fluid connection between the access holes and the irrigation plate wells. Said irrigation plate also has a multiplicity of wells, corresponding in number and position to the wells of the removably mounted netwell insert plate, wherein said wells are shaped to fit each corresponding hollow chamber of the netwell insert plate, and each irrigation channel of the corresponding access hole of said netwell insert plate, thereby resulting in a shape similar to the shape of the netwell insert plate well opening, but with a connecting inlet shaped to fit the irrigation channel, and to provide a fluid communication.

In another embodiment, the porous membrane of the multiwell plate system is characterized in that it is a hydrophilic mesh with a pore size of 400 µm to 600 µm.

Additional embodiments of the present invention relate to the shape or circumference of said netwell insert plate wells and access holes, wherein said circumference can be square, rectangular, rounded rectangular, oval rectangular, squircular, oval or circular. In another embodiment, said irrigation plate wells have an inlet to fit the netwell insert plate irrigation channel, and in addition to the inlet a well circumference that is square, rectangular, rounded rectangular, oval rectangular, squircular, oval or circular and fits said netwell insert plate hollow chambers, thereby providing a fluid connection between said irrigation channel and said hollow chamber when the netwell insert plate is mounted onto said irrigation plate. An alternative embodiment describes that said netwell insert and irrigation plate have an identical square, rectangular, rounded rectangular, oval rectangular, squircular, oval or circular circumference, with the exception that the irrigation plate wells have said additional inlet for fitting said irrigation channels within the same well of the hollow chamber fitting well.

Another embodiment of the present invention relates to a multiwell plate system characterized in that said netwell insert and irrigation plates contain 6, 12, or 24 wells.

In some embodiments, the multiwell plate system is made from at least two different types of materials, one to establish said porous membrane, and a second type of material for the plate body, wherein said material for the plate body is preferably a temperature resistant material. In another embodiment, said porous membrane material is a hydrophilic mesh, preferably polystyrene, and/or said plate body material is a non-transparent material, for protecting the plate content from light.

In another embodiment, said multiwell plate system is characterized in that the size and properties of said system are suitable for use of granular media in said hollow chamber. In some embodiments, said granular medium is characterized in that it is soil or a soil-containing mixture. And an alternative embodiment relates to a multiwell plate system for use in an in vivo screening assay wherein said screening assay applies granular media, or granular media comprising soil.

A second aspect of the invention relate to a netwell assay screening method for producing a compound, comprising the steps of:
(a) inserting a granular medium, preferably comprising soil, in the hollow chamber of said netwell insert plate wells;
(b) bringing in of the sample, preferably a plant tissue, seedlings or seed, in said granular medium of each well;
(c) mounting the netwell insert plate onto the irrigation plate;
(d) addition of irrigation solution via the access hole in said irrigation channel; optionally followed by sealing of the multiwell plate system over the edges
(e) treatment with test-compound-containing solution via the access hole without disturbance of the sample manually, or automatically using robotics.
(f) retaining the necessary soil humidity level by replenishing with said irrigation solution on frequent basis
(g) monitoring of compound treatment via evaluation of the sample in comparison to control sample In another embodiment, the invention relates to said method for use in a compound screening assay wherein said screening assay aims to identify compounds for improved plant characteristics, or in a more specific embodiment to identify compounds for improved plant yield.

BRIEF DESCRIPTION OF THE DRAWINGS

The drawings described are only schematic and are non-limiting. In the drawings, the size of some of the elements may be exaggerated and not drawn on scale for illustrative purposes.

*Arabidopsis* Rosette growth was determined as the Rosette area (y-axis) was measured over time (days after sowing (DAS) at x-axis) of *Arabidopsis* plants grown in the multiwell plate system upon treatment with a Stroby® solution containing 10-9 M Kresoxim-methyl ("Stroby"), a cytokinin solution containing 10 µM 6-Benzylaminopurine ("BAP"), and control water treatment ("water"). Eight plants (or wells) were used per treatment.

A, Netwell plate system of the current invention provides a volume to fit about 1.5 g of soil and stable humidity control B, Millicell (Millipore) plate system provides a volume to fit about 0.66 g of soil, resulting in more frequent watering needs and slower plant growth or lower plant yield.

*Arabidopsis* Rosette growth was determined as the Rosette area (y-axis) was measured over time (days after sowing (DAS) at x-axis) of *Arabidopsis* plants grown in the multiwell plate system using different types of soil, and control normal soil. One plate with 24 wells/plants were used per soil type.

A, for each plate, a different concentration or treatment was applied for each column. The experiment was repeated for at least 4 different plates, each with a different column position for the controls/concentration treatments. B, *Arabidopsis* Rosette growth was determined as the Rosette area (y-axis) was measured over time (days after sowing (DAS) at x-axis) of *Arabidopsis* plants grown in the multiwell plate system using different concentrations of NAA (1, 10, 20, and 100 µM; 50 µM was also tested, but left out since similar results were found as for the 100 µM wells), and control treatment with 0.1% DMSO.

*Arabidopsis* Rosette growth was determined as the Rosette area (y-axis) was measured over time (days after sowing (DAS) at x-axis) of *Arabidopsis* plants grown in the multiwell plate system upon treatment with a cis-cinnamic acid-containing (Cis-CA) solution at different concentrations (A), or a Paclobutrazol-containing solution at different concentrations (B), as compared to a control vehicle treatment ("0.1% DMSO").

DETAILED DESCRIPTION OF THE INVENTION

The present invention aims to provide a multiwell plate system which solves one or more of the aforementioned disadvantages of the use of the currently available multiwell plate systems for in vivo plant growth and screening. The present invention also aims to provide a method for growing samples, and in particular to perform in vivo compound screening assays, thereby solving one or more of the aforementioned disadvantages for high-throughput agro-chemical screening.

To solve the aforementioned problem for using a multiwell plate system for in vivo plant growth, at least one embodiment of the present invention adopts the following constructions as illustrated in the embodiments described below, some of which are also illustrated by the drawings. However, numerals affixed to respective elements merely exemplify the elements by way of example, with which it is not intended to limit the respective elements. Before the present device and method of the invention are described, it is to be understood that this invention is not limited to particular devices and methods or combinations described, since such devices and methods and combinations may, of course, vary. It is also to be understood that the terminology used herein is not intended to be limiting. The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein. The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); Ausubel et al., Current Protocols in Molecular Biology (Supplement 114), John Wiley & Sons, New York (2016), and Pessarakli, Handbook of plant and crop physiology (2014) for definitions and terms of the art. The definitions provided herein should not be construed to have a scope less than understood by a person of ordinary skill in the art.

The recitation of numerical ranges by endpoints includes all numbers and fractions subsumed within the respective ranges, as well as the recited endpoints.

The present invention provides a device and a method allowing to uninterruptedly grow plant tissue for high-throughput in vivo screening assays using a multiwell plate system with a dual well architecture, adapted to obtain reliable stable growth conditions for solid support media. In particular, the multiwell plate system allows plant tissue growth in granular media, such as soil, protected from light, in large enough volumes to allow robust plant growth, reliable humidity control, and with the possibility of automated, undisturbed addition of nutrient solution or compound treatments without resulting in difficulties in handling or inhomogeneous distribution of the liquid solutions to the samples.

Figure 1:
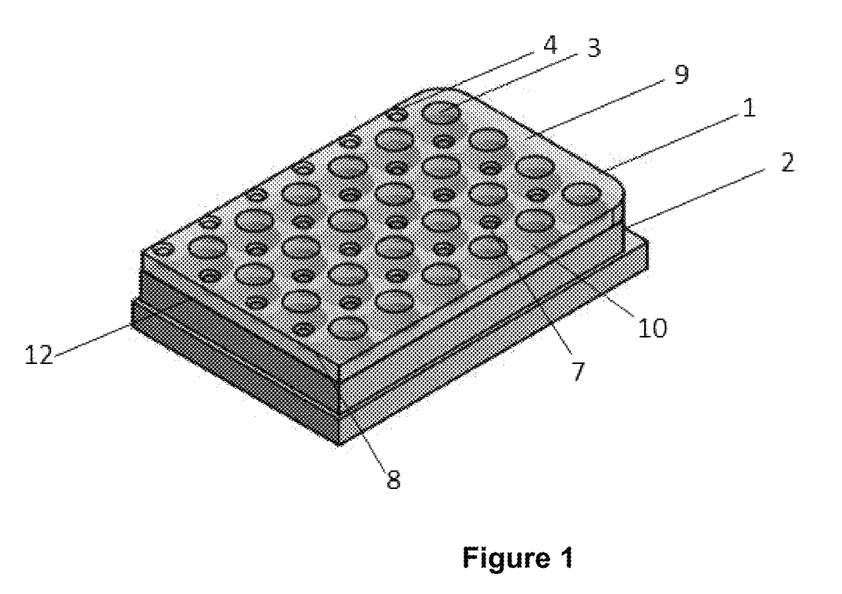
FIG. 1 depicts a bird's-eye view of the multiwell plate system according to one of the embodiments of the present invention.
Figure 2:
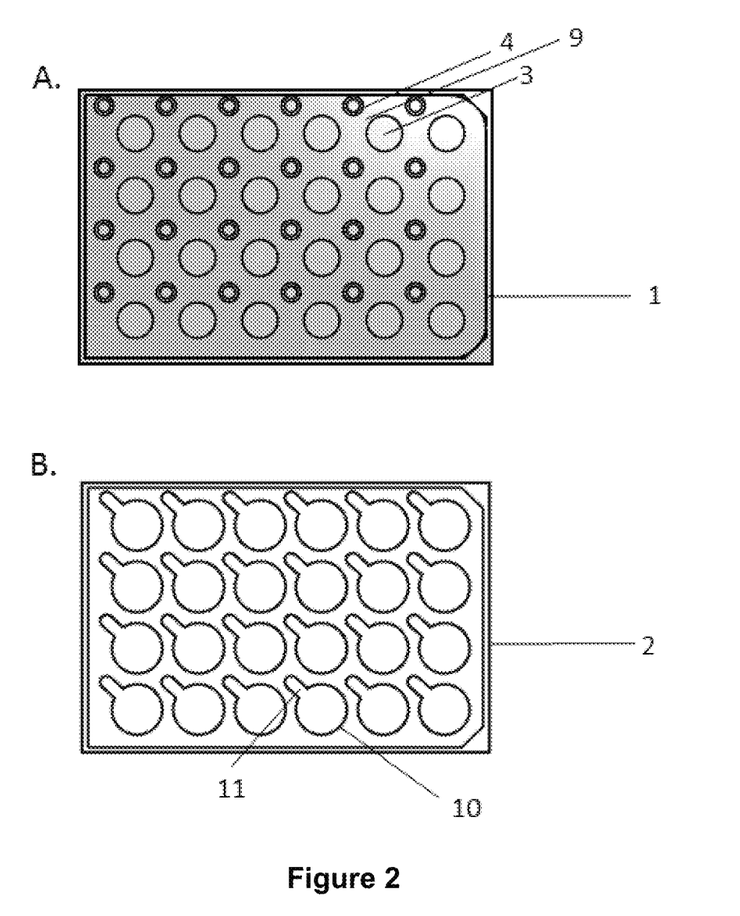
FIG. 2 depicts a bird's-eye view of the top netwell insert plate (A) and the bottom irrigation plate (B) according to one of the embodiments of the present invention.
Figure 3:
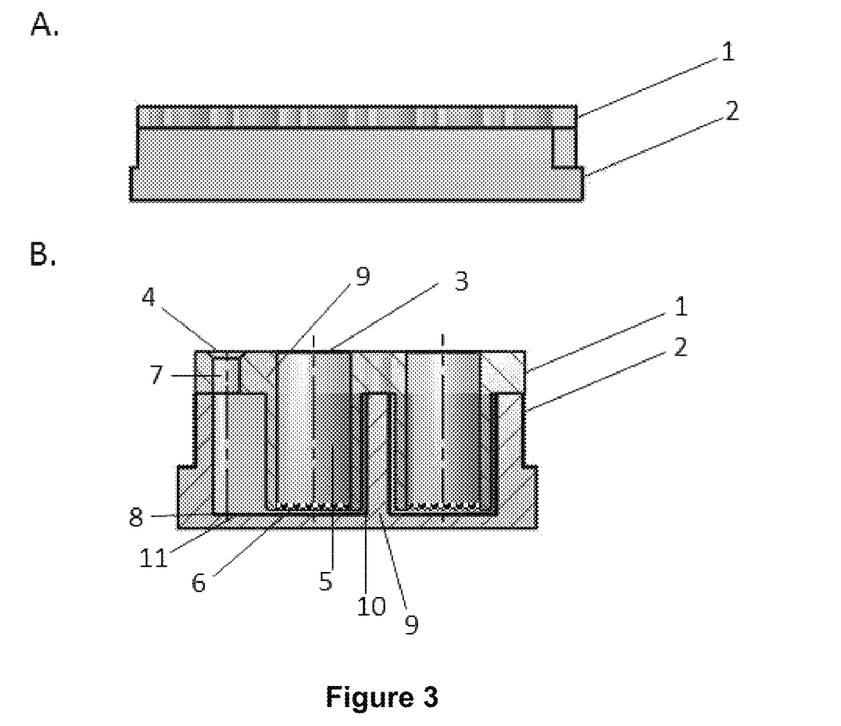
FIG. 3A depicts a side view of the multiwell plate system according to one of the embodiments of the present invention.
FIG. 3B depicts a cross section of the multiwell plate system according to one of the embodiments of the present invention.

In a first aspect, the present invention provides in a multiwell plate system comprising a top netwell insert plate (1) and a bottom irrigation plate (2), mounted onto each other, having a multiplicity of wells, and including a plate body (9). The plate body of the netwell insert plate defines an array of well openings or sample holes (3), and an arrangement of access holes (4), as shown in FIG. 1 and FIG. 2. Inwardly from said well openings, a hollow chamber (5) is present to house the supportive medium, and is secured in the bottom by a permeable barrier or porous membrane (6), which has a pore size ranging between 200 µm and 1000 µm, to allow support to a tissue sample residing in said supportive medium, particularly a granular medium (FIG. 3). As used in the present invention, the term "well" used for said netwell insert plate refers to a combination of a "well opening" or "sample hole" defined in the plate body, and an inwardly connecting "hollow chamber" to constitute the sample support. Inward from the access holes of the netwell insert plate, an irrigation channel (7), which is connected with the access hole, connects the access hole further through the bottom of the netwell insert plate, where an open ending (8) is present, to allow solution added via the access hole to arrive in the irrigation plate well when the plates are mounted onto each other (FIGS. 1 and 3). Each of the respective one of the netwell insert plate wells (3) is accompanied by an adjacent one of the access holes (4), and therefore each of the hollow chambers also accompanied by an irrigation channel, as shown in FIG. 3B. In the upper netwell insert plates, the access hole is not in connection with the well opening, so the access hole is adjacent but separated from the wells by the plate body, wherein "adjacent" is defined as "nearby" "adjoining" the well, but not in connection with the well via the insert top plate, in such a way that the plate surface is built up of an array of well openings which are all in a similar configuration close to an access hole. The irrigation plate also comprises a number of wells (10), corresponding to the number and position of the wells of the netwell insert plate, but with a shape which fits the corresponding hollow chamber of the corresponding netwell insert plate well, in addition to its adjacent irrigation channel (FIG. 1, 2B, 3). This requirement leads to a shape of the irrigation plate wells containing an inlet (11), as demonstrated also in FIGS. 2B and 3B.

When the multiwell plate system is in a mounted position, i.e. netwell insert plate and irrigation plate are fit together (as shown in FIG. 1), and in one embodiment the plates are sealed to avoid desiccation via the edges (12), the hollow chamber with its porous membrane will be housed in a reservoir or well of the irrigation plate (10), which is in one embodiment filled with liquid solution, added via the access hole and passing the irrigation channel. The porous, hydrophilic properties of the membrane will allow the solution to move upwards via capillary forces into the granular medium present in the hollow chamber, as in some embodiments, so as to supply the irrigation solution to the granular medium, and hence to nourish the tissue sample placed in the granular media housing in the hollow chamber.

To further outline said multiwell plate system, the applied terms are further defined as follows. The term "mounted" means that to form the multiwell plate system, the top netwell insert plate is placed onto the upper side of the bottom irrigation plate. In one embodiment, the top netwell insert plate is removably mounted onto the irrigation plate. In another embodiment, the top netwell insert plate is mounted onto the irrigation plate, followed by sealing over the edges. This advantageously avoids drying out and inhomogeneous conditions in the samples from different wells, more particular stable humidity control is achieved, thereby providing a screening device to deliver reproducible data as taught herein.

The "access holes" (4) extend through the upper surface of the netwell insert plate body and the term refers to providing access to single wells (10) in the irrigation plate into which also the hollow chamber of the netwell insert plate is positioned when the multiwell plate system is in a mounted position. Each of the access holes is preferably adjacent to a netwell insert plate well opening, and connected in fluid communication with a respective one of the irrigation plate wells. As shown in FIGS. 1 and 3B, water, nutrient or treatment solution can be introduced manually through access holes with a conventional liquid handling device, such as a syringe or a pipette, or automatically via robotics, to end in the irrigation plate well. The shape and size of the access holes can have larger or smaller diameters, and different center-to-center distances could be used, depending upon the size of the pipette tip to be inserted therein. Of course, other shapes and other dimensions could be varied to suit a customized arrangement, or other standard pipette shapes and lengths that are known to those of skill in the art. Circular access holes are easiest to apply automated handling. The center-to-center distance between adjacent ones of the access holes is preferably the same as the center-to-center distance between the wells, which is 1.93 cm in the illustrated embodiment of 24 wells. The pairing arrangement of the access holes and the wells allows addition of any solution individually to each well, without cross-contamination of the samples, and without disturbance of the biological samples or removing of any of the plates. In addition, the pairing arrangement allows the solutions to be different in concentration, amount and compound to test for each individual well selectively. Selectively addressing wells would be useful if, for instance, the tissue in one of the wells was generating a strong expression response to an agent, such as increased growth of tissue, increased expression of a polypeptide, added resistance to a selective agent such as a herbicide, or resistance to a plant pathogen. Other biochemical or biophysical responses could also be assayed in individual wells with the present invention. The media from this well could be irrigated and tested more frequently than the other wells. Among other advantages, more frequent collection and testing of media from that well would provide a stronger statistical correlation. An "irrigation channel" (7) as taught herein is the inwarding volume following the access holes, wherein each of the irrigation channels connects a respective pair of the netwell insert plate wells and access holes in fluid communication, as shown in FIG. 3B. Each of the irrigation channels is preferably roughly of similar shape as the access hole, and is separated from the hollow chamber by the netwell insert plate body. The irrigation channels end in an opening (8) in the bottom, where, when mounted onto the irrigation plate, the applied solution in the access hole, will be passed through the irrigation channel to end up in the corresponding irrigation plate well. In addition, each of the irrigation channels act, along with its respective one of the wells and the access holes, as a reservoir for excess irrigation solution that has not been taken up over the porous membrane in the hollow chamber media. Preferably, the width of each of the irrigation channels is less than the diameter of its respective one of the wells so as to end in an inlet at the bottom of the irrigation plate well.

The term "hollow chamber" (5) used herein teaches as the volume following the netwell insert plate well openings, as illustrated in FIG. 1 and FIG. 3B. The shape is corresponding to the shape of the netwell insert plate wells, and in order to create an overflow region in the irrigation plate, the height of the hollow chamber is preferably smaller as compared to the sum of the height of the netwell insert plate and the irrigation plate wells, preferably said hollow chamber height is 5%, 10%, 20%, or 30% smaller in height compared to the sum of the height of the netwell insert plate and the irrigation plate wells to allow enough volume for the irrigation solution within the irrigation plate wells.

The hollow chamber is interchangeably called a "sample holder" as the biological sample is placed herein. In one embodiment, the hollow chamber is first filled with sample support media, such as granular media, preferably soil. Irrigation of the sample, via capillary forces through the porous membrane and the granular media, is accomplished when the multiwell plate system is mounted and irrigation solution is added via the access hole to reach the irrigation plate wells via the irrigation channel. Alternatively, the irrigation plate can be filled with irrigation solution prior to mounting of the netwell insert plate onto the irrigation plate, which will also allow the tissue that is present in the hollow chamber to be irrigated after mounting the netwell insert plate onto the filled irrigation plate. The volume of the hollow chamber can vary according to the type of samples and media, as well as to the type and size of the experiment. The exemplified 24 well system provides a non-limiting example of an appropriate hollow chamber volume to fill with approximately 1.5 g of soil, which is at least twice the amount of the amount of soil that can be filled in the currently existing systems (e.g. 0.66 g in the 24 well Millicell plates from Millipore), thereby allowing a more reliable and robust humidity control requiring lower irrigation frequencies as compared to other plate devices, and providing more suitable growth environment (see Example 3 and FIG. 5).

The term "permeable barrier" or "porous membrane" can be used interchangeably and refers to a barrier that is permeable to liquid solutions but not particulate materials, such as granular media, over the rated pore size. Porous membranes may be formed in a variety of shapes, and is within each well, where it holds the granular media in its interstices, allowing contact between the media and the solution applied via the access holes. By housing supporting granular media on the porous membrane in the hollow chamber, anaerobic conditions are avoided for the added samples, and the solution provided in the irrigation plate is able to pass upwards in sufficient quantities via capillary forces to provide nutrients to the sample and promote proliferation of the tissue. Each porous membrane is constructed of a (synthetic) polymer such as a plastic (e.g. polypropylene, polyethylene, or polystyrene). In particular embodiments, the porous membrane is a hydrophilic mesh, which means consisting of a hydrophilic material appearing as a net with spaces in it, made from wire, plastic, or thread, wherein said mesh is made from polystyrene in a particular embodiment. The polystyrene material is porous and hydrophilic to promote the attraction and retention of the media within its interstices. In another embodiment, the hydrophilic material of the mesh is not polyester. In another embodiment, the porous membrane is hydrophilic, and not polycarbonate. The hydrophilicity of the porous membrane can be permanent or temporary depending upon the processes by which it is applied, or whether the material is inherently hydrophilic. Alternative materials with porous structures could be used and a surfactant could be applied to materials not naturally hydrophilic to make them hydrophilic. The material is produced by sintering and allows solutions to pass upwards through the pores by capillary action.

The range of the pore size of said porous membrane surprisingly determined whether the system of watering via the irrigation channel would function to obtain a robust humidity. Although the Millicell Millipore system provides membranes with a small pore size (up to 8 μm for a 24 well plate), which are capable of housing granular media inside the hollow chamber, the desired effect of capillarity of a watering solution added via the access hole into a granular medium such as soil is less effective using this system, i.e. when a porous membrane with a small pore was used (Example 3). Surprisingly, when a mesh with a larger pore size, above 200 μm was used, as exemplified with the system of the invention (see Examples), watering via the access hole was possible due to the possibility of fast capillarity through the pores, over the membrane, into the granular medium. Therefore, the invention describes a porous membrane with an average pore size in a range of 200 to 1000 micrometers, wherein the exact pore size and the allowable range is defined by the capability of the pores to retain a certain type of granular media, such as soil, and so that the pores still allow liquid solutions, such as water, to be passing through the pores via capillary forces. In another embodiment, the pore size is in a range of about 250 to 900 μm, of about 300 to 800 μm, of about 350 to 700 μm, of about 400 to 600 μm, and in a preferred embodiment, the pore size is between about 400 and 500 μm, for use of granular medium such as soil. The pore size can be adapted within said ranges depending on the type of granular medium, as the "grain" or "particle" size of the medium will define the allowable pore size range in which the medium will be retained, and liquid solution is passing through.

The term "granular medium" refers to a material showing a granulated structure, composed of granules, made of or appearing to be made of small pieces or granules. A granular material is a conglomeration of discrete solid, macroscopic particles large enough that they are not subject to thermal motion fluctuations. Some examples of granular materials are coal, sand, rice, coffee, and soil. With "granular medium", the present invention teaches hence such defined media, with in particular, examples of media to grow plant tissue, such as sand, perlite, vermiculite, and all classes of granular soil. Soil is defined as the top layer of the earth's surface in which plants can grow, consisting of rock and mineral particles, mixed with decayed organic matter and having the capability of retaining water. A granular soil medium hence comprises sediments or other unconsolidated accumulations of finely ground rock particles in addition to minerals. Different soil types are distinguished, based on their texture or different sizes of mineral particles. For example, the largest particles, sand, determine aeration and drainage characteristics, while the tiniest, sub-microscopic clay particles, are chemically active, binding with water and plant nutrients. The ratio of these sizes determines soil type, of which there are many classifications: clay, loam, clay-loam, silt-loam, peat, chalky soil, and so on. A granular medium is also defined as a mixture of any of those granular media and any of those materials comprised in soil.

According to one embodiment, the use of the multiwell plate system is exemplified with reference to FIGS. 1, 2 and 3. As shown in FIG. 1, the netwell insert plate of the multiwell plate system is positioned on top of the irrigation plate, both including a multiplicity of wells, such as 24 wells that are corresponding in number and size and location. The irrigation plate together with the access holes to the irrigation channels may be used as a watering system or it may be used in a screening assay, such as in compound assay studies to supply treatment solution. In use, the multiwell plate system is mounted as such that a hollow chamber, secured by a porous membrane in the bottom, extends into only one well of the irrigation plate, with a relative position of the center of each hollow chamber corresponding to the center of each irrigation plate well. Each of the netwell insert plate wells has associated therewith an access hole which permits access to an irrigation plate well of the multiwell plate system utilized during a sample assay step. In another embodiment, the multiwell plate system as described herein provides that said multiwell plate system is made from a combination of at least two different types of material, one material constituting the porous membrane, as described above, and the second material constituting the plate body, wherein said second material is preferably resistant enough to heat to be sterilized in an autoclave for reuse.

In another embodiment, the second material constituting the plate body is made from non-transparent or non-light transmissible material, to protect the irrigation solution and/or sample holder, or plant roots from light.

The multiwell plate system's non-transparent plate body in particular protects roots, housing media, and irrigation solution from light or UV, which is advantageous when performing experiments over a longer time in non-sterile (in vivo) conditions to avoid growth of algae, fungi, and to maximally mimic the natural environment.

As used in the present invention, the term "plate body" refers to the solid material of the multiwell plate system that is annotated as a diagonal pattern in FIG. 3B, and is made of, for example but not limited to, a plastic block that can be machined. Generally, the hardness of the material defines whether it will allow to be machined by computer controlled milling machine, or other automatic machining process, into complex, precision shapes. The plate body could be constructed of different materials, such as a polystyrene, polysulphone, polyoxymethylene (POM), epoxy, vinylester or polyester thermosetting plastic, or high or low density polyethylene. Other examples of suitable material include synthetic rubber, such as styrene ethylene butylene styrene (SEBS), or thermoplastic elastomers (TPE), such as styrenic block copolymers (TPE-s), polyolefin blends (TPE-o), elastomeric alloys (TPE-v or TPV), thermoplastic polyurethanes (TPU), thermoplastic copolyester, metals, ceramics, glass, amongst others.

The height of the multiwell plate system plate body ranges between about 10 mm and 100 mm, preferably between about 20 mm and 50 mm, more preferably between about 25 mm and 30 mm, such as for instance about 26.45 mm. The plate shape is rectangular, with a length of for instance 127.65 mm for standard well plates. The plate body has a flat upper surface through which the access holes and wells are drilled. It should be noted, that although the size of the body is preferably configured for compatibility with preexisting equipment, the dimensions of the body can be varied as desired, allowing easy and sufficient growth of plant tissue from different plants or crops.

With the expression "sample", "biological sample", or "tissue sample", as used interchangeably, is meant herein "a sample obtained from a biological source", with preferably "plant tissue", "plant sample", "seedling" or "seed" meaning a biological source of plant material. The biological sample may be obtained for example, but without limitation, from plant material such as from dicot and monocot plants or plant tissue from for instance *Arabidopsis thaliana, Medicago truncatula*, corn (*Zea mays*), *Brassica* sp., alfalfa (*Medicago sativa*), rice (*Oryza sativa*), sorghum (*Sorghum bicolor, Sorghum vulgare*), wheat (*Triticum aestivum*), soybean (*Glycine max*), tobacco (*Nicotiana tabacum, N. benthamiana*), potato (*Solanum tuberosum*), tomato (*Solanum lycopersicum*), cotton (*Gossypium barbadense, Gossypium hirsutum*), sugar beets (*Beta vulgaris*), and sugarcane (*Saccharum* spp.), amongst others. In another embodiment, also the number, shape and size of the wells depends on the type of sample applied.

It will be understood by a skilled person that the number, size and shape of wells depends on the type of sample that needs to be analyzed and the number of experimental tests that needs to occur. Therefore, the multiwell plate system according to the present invention may comprise between 2 and 24 wells. Preferably said multiwell plate system comprises 6, 12, or 24 wells. The number, dimensions and locations of the wells are also tailored to be compatible with preexisting equipment. For instance, the plate preferably has 24 wells in an array of 4 by 6, or 12 wells in an array of 3 by 4 to be compatible with most liquid handling devices. Other well densities could be used such as 6 wells, that are compatible with conventional devices. However, nonstandard well densities could also be used, such as two wells, 3, 4, 5, 7, 8, 9, 10, 11, 13, 14, 15, 16, 17, 18, 19, 20, 21, 22 or 23 wells. Generally, the number of wells will be limited by such practicalities as the size of the plate body, the type of sample, the capabilities of the equipment using the wells and the required size of the wells themselves, the required liquid solution volume, and so on.

According to another embodiment, the multiwell plate system according to the present invention provides that said wells of said netwell insert and/or said irrigation plates have a square, rectangular, rounded rectangular, oval rectangular, squircular, oval or circular circumference. The circumference or edge of said wells refers to the shape of the rim of the wells that makes contact with the plate body of the multiwell plate system. Preferably, said shape is rounded rectangular, oval rectangular, oval or circular. In a preferred embodiment, said irrigating plate wells have in addition to the well shape, an additional inlet, as provided in FIG. 2B, to fit the irrigation channel inserted from the netwell insert plate when both plates are mounted onto each other. The shape of the wells is chosen as such that they are suitable for the particular plant tissue samples and supportive media of interest, and the well size are compliant to the experimental setup (i.e. depending on the analytical purpose of the assay). This facilitates the handling of the samples, maintains highly robust conditions and provides a high degree of standardization. As illustrated in FIGS. 1 to 3, each of the wells has a standard circular shape for the 24 well plate. In a particular embodiment, the 24 well plate has been determined by the inventors to be particularly suitable to the seedling propagation of *Arabidopsis* seeds/seedlings, over a period of 14 days after sowing, presenting a preferred balance of tissue volume and density of wells. The density of the wells used for other plant types can be less or more due to the size of the plant and duration of the experiment/growth phase. For instance but not limiting, the density of the wells for wheat, tomato or maize seedlings will become lower due to a larger size of those type of plants as compared to *Arabidopsis* plants after growth for a certain number of days.

In another aspect, the present invention provides in the use of the multiwell plate system according to the present invention for an in vivo screening assay for uninterruptedly growing of plant tissue, wherein said hollow chamber of the netwell insert plate contains a granular medium serving as a solid sample support, such as soil in one particular embodiment. The device provided by the present invention allows a person skilled in the art for the first time to immediately perform high-throughput compound screenings in natural substrates such as granular media, and applying more optimal conditions (e.g. roots protected from light, no oxygen deprivation, and stable humidity control) thereby avoiding lengthy in vitro selection procedures including additional risks of identifying false positives.

An in vivo screening assay, wherein plant samples are growing supported by granular media and nourished with nutrition solution applied via the access holes, in addition allows to identify new compounds that affect plant growth and development. When a treatment solution is applied, in the same manner as the nutrition or watering solution is applied, the effect of the treatment can be monitored over time, in several ways, such as by imaging analysis.

A "compound" or "test compound" is defined herein as any chemical or biological compound, including simple or complex organic and inorganic molecules, small molecules (e.g. growth regulators or hormones), peptides, peptidomimetics, proteins, antibodies, carbohydrates, nucleic acids or derivatives thereof, biologicals, bacterial isolates, all derived synthetically or from natural resources. The term "treatment" or "treating" or "to treat" can be used interchangeably and is taught in the present invention as application of a "treatment solution" to a sample or well, in which the treatment solution contains said test compound, with the aim to test the impact of the treatment solution on the progression of plant sample development or growth in a certain condition.

In a further aspect, the present invention provides in a netwell assay screening method for producing a compound, comprising several steps, in one embodiment initiated by inserting a granular medium, preferably soil, in the hollow chamber of said netwell insert plate wells; followed by bringing in of the sample, preferably plant tissue, seedlings or seed, in said granular medium of each well; mounting the netwell insert plate onto the irrigation plate; addition of irrigation solution via the access hole in said irrigation channel; followed (optionally) by sealing of the multiwell plate system over the edges; incubation of the plant tissue until treatment is desired, including the necessary provision of watering or nutrient solution on a regular basis; treatment with test-compound-containing solution via the access hole without disturbance of the sample, manually or in some embodiments automatically, using robotics. Finally, retaining the necessary soil humidity level is done by replenishing with irrigation solution on frequent basis, and monitoring of compound treatment over time is performed through evaluation of the sample in comparison to a control sample. A control sample is defined as a reference standard sample, meaning that the same tissue is used, but treated with an irrigation solution that does not contain the testing compound, or that contain an inactivated test compound or vehicle control. Alternatively, a control sample could also be a sample well which receives the same treatment as the samples or wells of interest, but differs from the other samples in genetic background, species, type, or age. Another option is that the control sample uses another type of granular medium, such as for instance a rich or poor type of soil.

In an alternative embodiment, said method is applied for use in a compound screening assay wherein said screening assay aims to identify compounds for improved plant characteristics or more particular improved plant yield, which can be evaluated for instance as exemplified below, but also in different manners, and by different phenotyping analytical methods, depending on the goal of the assay. A person skilled in the art is supposed to define a suitable evaluation procedure to define when a compound can be identified as being a candidate for improving plant characteristics, or plant yield, based on the result of the screening assay.

An improved plant characteristic or plant performance is described herein as a plant breeding being improved as compared to a wild-type variety of the plant. So preferably, improved is determined relative to the characteristics in a control plant, or a control treatment. Examples of different plant characteristics improved by the identified compound or the resulting improved plant performance include increased root growth, increased seedling vigor, increased or decreased branching, resistance to oxygen stress/hypoxia; tolerance to abiotic stresses in general, and more specific to drought conditions or heat; improved water use efficiency; lower stomal density and/or index; increased or decreased hormone sensitivity, resistance to biotic stress, amongst others.

In one embodiment, when nutrient supply is performed automatically, the multiwell plate system is loaded on the liquid handling device of choice to replenish the irrigation solution via the access hole in hollow chamber. The liquid handling device extends each pipette tip into a respective one of the access holes, providing the necessary amount of solution through the irrigation channel. The irrigation solution volume is supplied as often as needed by repeating the above process. In another embodiment, an automated pipetting head (or robotic liquid handler) is used to address single or multiple wells selectively. The tips of the robot are configured to deliver irrigation solution or treatment solution to a plurality of wells on multiple multiwell plate systems at once. Preferably, a robotic liquid handler is operated using a software program to control deployment of its pipetting tips in such a way as to minimize cross-contamination between the wells.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

FIG. 1 illustrates the Multiwell Plate System.

The multiwell plate system comprises the upper netwell insert plate (1) and the bottom irrigation plate (2), which can be mounted together to obtain a closed in vivo growth and screening system.

The upper netwell insert plate contains 24 wells (3), each well accompanied by a corresponding access hole (4), which allows the addition of a solution to the wells. When a certain amount of solution is added via the access hole (4), it will pass through the irrigation channel (7) to the bottom of the netwell insert plate, which is an opening (8) being in contact with in the corresponding irrigation plate well (10).

FIG. 2 illustrates the Upper Netwell Insert Plate (A) and Bottom Irrigation Plate (B) of the Multiwell Plate System.

The upper netwell insert plate top view depicted in FIG. 2A demonstrates that all individual well openings (3) are accompanied by an access hole (4), and equally distributed among the plate surface, to allow maximum space for each sample. The access holes are not connected to the individual well openings in the upper netwell insert plate, but separated by the plate body (9). The bottom irrigation plate top view as depicted in FIG. 2B shows that each well (10) is shaped in such a manner that an inlet (11) is present to receive the solution from the accompanying access hole/irrigation channel. In this way, in the bottom irrigation plate, each of the wells is in connection with the separate inlet area, to provide a connection between the irrigation channel and the receiving hollow chamber of the corresponding netwell insert plate well.

FIG. 3A Shows a Side View of the Multiwell Plate System.

In FIG. 3A, the upper netwell insert plate (1) is only visible as a thin bar (dashed grey fill), since most of the insert plate is mounted and inside of the irrigation plate (2). The irrigation plate is visible as the bottom bar (equal grey fill), and is designed to allow mounting of the insert plate, and retaining enough space in the bottom of the wells to receive solutions to be provided to each of the insert well opening through capillary forces through the porous membrane into the granular medium of the hollow chambers of the netwell insert plate wells.

FIG. 3B Shows a Cross Section of the Multiwell Plate System.

In FIG. 3B, the distinct features of the upper netwell insert plate (1) and bottom irrigation plate (2) are visible and annotated for the left well in the image: the insert plate well opening (3) ends inwardly as a hollow chamber (5) in which the granular medium will be housed, and which is secured in the bottom by a porous membrane (6) consisting of, for instance, hydrophilic mesh. The access hole (4) accompanying the insert plate well opening, allows solution to be added to the samples as the solution added to the access hole will pass through the irrigation channel (7) of the netwell insert plate, to end up in the bottom opening of said insert plate (8). The wells (10) of the irrigation plate (2) are corresponding in size and shape to fit the insert plate hollow chamber, with in addition an inlet (11), to fit the irrigation channel of the netwell insert plate and receive the solution added via the access hole, as a fluid communication is maintained between the irrigation channel and the hollow chamber via said irrigation plate wells when the plates are mounted. The plate body (9), consisting for instance of plastic material, is annotated as a diagonal pattern, with lines going right upward for the irrigation plate body, and going left upward for the insert well plate body. The dashed vertical lines are not part of a feature, but only illustrating the center of the wells and irrigation channel.

Example 1. Netwell Assay Growing and Compound Screening Method

Germination, Growth and Treatment of Plant Samples

In the *Arabidopsis* netwell growth assay, plants were grown in soil inside a 24 well netwell insert plate comprising a polystyrene porous membrane with a pore size of about 420 µm, which is positioned into a 24 well irrigation plate (FIG. 1, 2).

Before sowing, seeds were vernalized in water at 4 degrees Celsius for two days. Afterwards, the netwell insert plate was filled with fine potting soil, or optionally with soil mixed with sand (ratio 3:1). During this process the soil (or soil with sand) was compressed two times (or optionally three times for soil/sand) by applying a light pressure onto the individual netwells.

A "humidity control" soil sample was taken for determination of the initial soil water humidity (see later). Next, one mL of water was added to each of the wells of the irrigation plates. The netwell insert plates were positioned inside the irrigation plates and the mounted plates were sealed with (plastic) tape surrounding the edges, to prevent excessive water evaporation from the boundary wells as compared to the center wells of the 24 well plate. This was a crucial step to avoid growth differences between plants in boundary and center wells, and to obtain reproducible results. Next, the weight of the combined insert and irrigation plates was recorded.

When seeds were used as samples, during the sowing of the *Arabidopsis* seeds, one seed was distributed in each of the wells. For germination, the netwell insert plates were covered with a standard multiwell cover plate which was sealed with parafilm and was placed inside a plant growth chamber. After three days, the covers were removed and the plants continued to grow at normal atmospheric conditions.

When seedlings or other plant tissue were used as samples, they were potted into the soil, and immediately grown in atmospheric conditions.

At 7 days after sowing, or when the appropriate plant stage was reached (e.g. 7 and 10 or 5 and 7 days), the plants received a (chemical) treatment. Therefore, 0.5 (optionally 0.8 mL for soil with sand) of a (chemical-containing) solution was added to each of the wells via the corresponding access holes. Each plant sample receives the supplied (same) amount of (chemical) solution. In the days following the treatment, the plants were again irrigated with water to maintain a soil water humidity of 3.5 (or optionally 0.95 for soil with sand) (see below). In the 24 well format the growth of *Arabidopsis* plants was typically followed for about 15 days, during which image analysis procedures were used to follow the growth of the individual plant samples over time and to quantify the growth response of these plants in response to the specific (chemical) treatments.

Soil Water Humidity Determination and Watering

The initial soil water humidity was determined by first drying the "humidity control" soil sample in an oven at 60 degrees Celsius, to obtain the "dry weight". Next, taking into account the weight of the empty irrigation plates, the empty netwell insert plates, and the current weight of the combined insert and irrigation plates, water was added to each of the wells to reach a "soil water humidity" of "3.5 gram water per gram of dry soil" or "3.5" (optionally, when soil with sand was used: "0.95 gram water per gram of dry soil (with sand)" was used as initial soil water humidity value). Water was added into the irrigation plate wells through the access holes present in the corresponding netwell insert plate wells using a repetition pipet. Due to equal evaporation of water from individual wells within one insert plate, each well of the irrigation plate received the same amount of water, rounded to 100 µL. The water, added to the wells in the irrigation plates, is taken up by the soil present in the hollow chambers of the netwell insert plate wells, through the mesh by capillary forces (FIG. 3B). This irrigation was repeated on a daily basis to prevent excessive drying of the soil in the wells. This watering regime is suitable for frequently used *Arabidopsis* growth conditions, but can be altered and further optimized when a plant drought-stress response is the desired testing regime.

Optional: Cleaning and Re-Use of the Netwell Plate System

First, most soil is removed by hitting the plates against each other. Then the plates are soaked in water over night and the remaining soil and other remnants attached to the walls of the individual wells are removed by using brushes. If the porous membrane at the bottom of the hollow chambers is damaged or remains dirty, they can be replaced with a new membrane.

Figure 4:
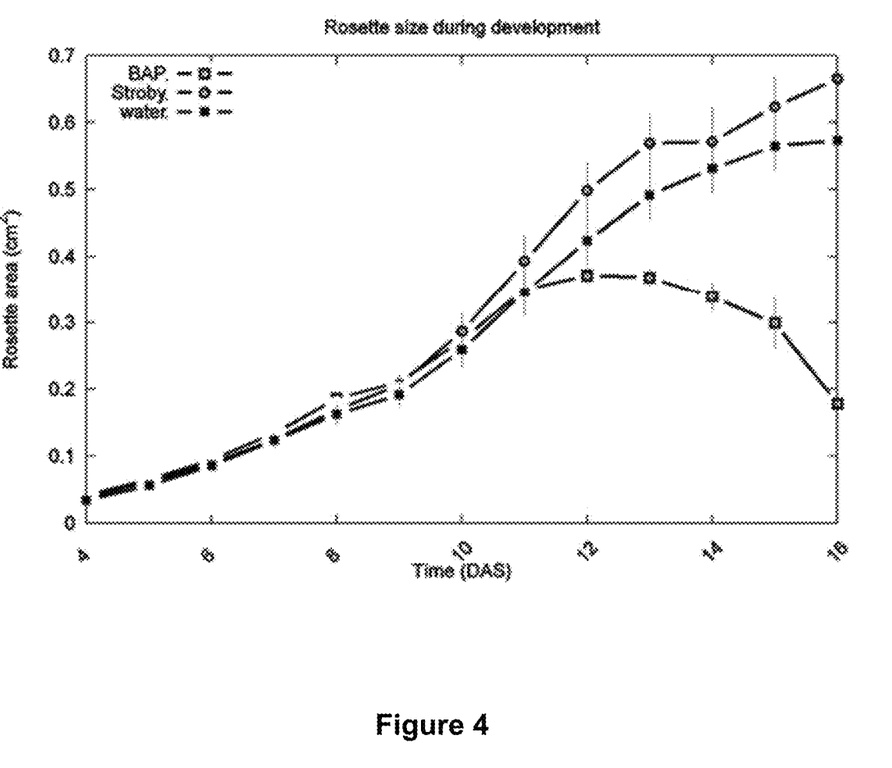
FIG. 4: *Arabidopsis* in vivo growth and compound testing using the netwell assay.

Example 2. Compound Testing for Enhanced *Arabidopsis* Growth in the Netwell Assay Plants were grown as described in the above Netwell assay method. At 8 days after sowing (DAS) 0.5 mL of treatment solution was added to each of the wells, with n=16 plants or wells per treatment. The different treatments comprise a) a Stroby® solution containing 10 µM Kresoximmethyl (FIG. 4, "Stroby"), b) a cytokinin solution containing 10 µM 6-Benzylaminopurine (FIG. 4, "BAP"), and c) water as a control treatment (FIG. 4, "water"). Growth of individual plants was followed over time by daily imaging between 4-16 DAS. Projected rosette sizes were measured using image analysis procedures. Average rosette areas were calculated over time per treatment (FIG. 4). Treatment with the Stroby® solution showed a plant growth enhancing effect, whereas the cytokinin application resulted in shoot growth inhibition (FIG. 4).

Example 3. Netwell Assay Method Using Millicell Cell Culture Plate (Millipore)

In first instance, the available system of Millipore for in vitro cell culture was tested for its use in in vivo plant screening, starting with water irrigation. The Millicell 24 cell culture insert plate system (PSET010R5), with a pore size 8 µm, was assembled, and watering solution was added via the access port of the system.

The hollow chamber volume for soil was determined in the Millicell 24 cell culture insert plate to fit about 0.66 g of soil, whereas in the netwell plate system of the invention, the hollow chamber fitted about 1.50 g of soil, which is about double the amount for the same amount of wells in the same plate size.

Figure 5:
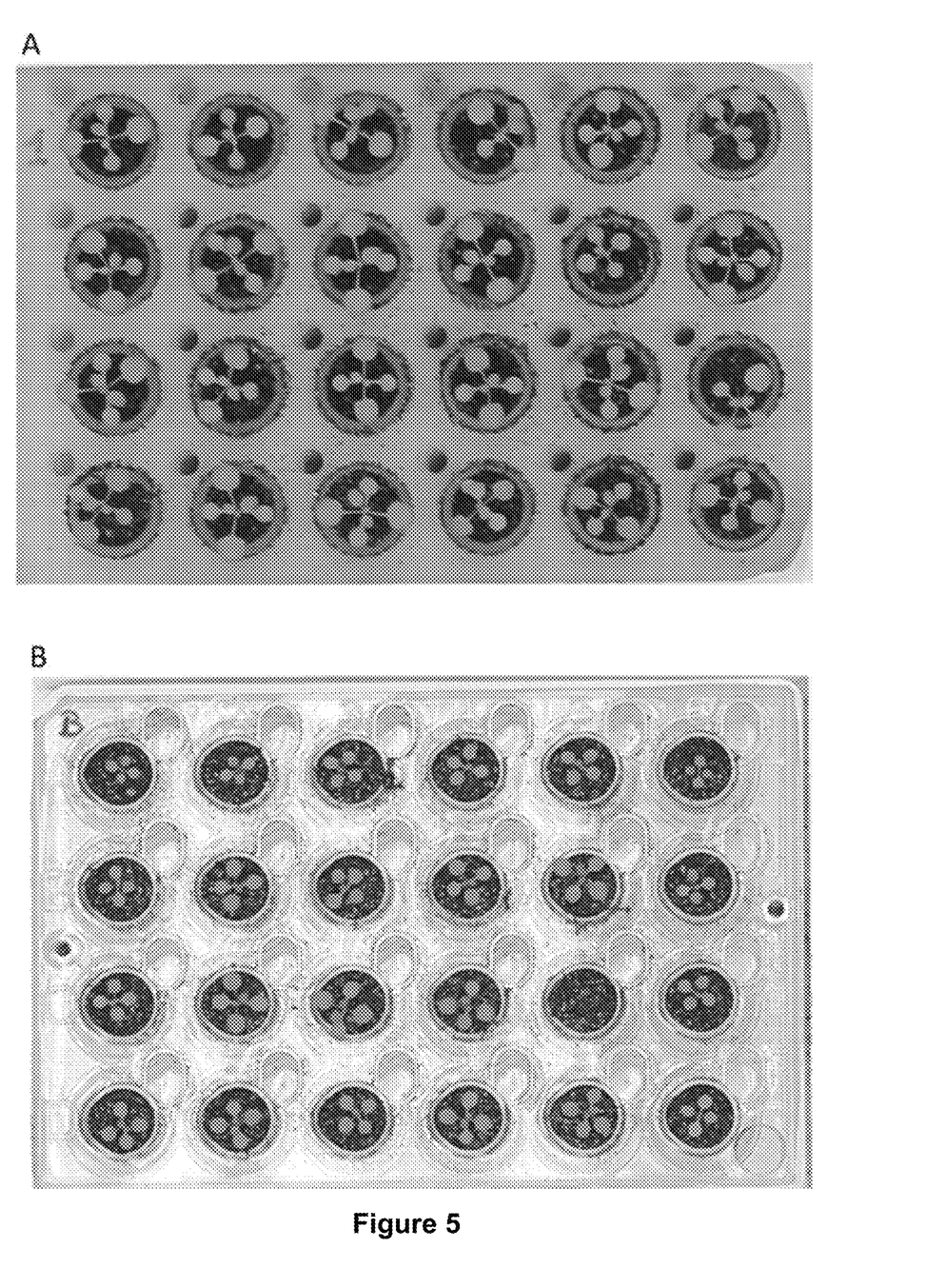
FIG. 5: *Arabidopsis* in vivo growth 13 DAS

The advantage of the system of the current invention is that the bigger pore size of the membrane and the larger volume of medium housing the hollow chamber surprisingly provided more optimal growth conditions, most likely due to more stable humidity control and less frequent need for watering, resulting in larger plantlets, and hence more robust and reliable results (FIG. 5).

Therefore, further development of the netwell assay method for granular media applications was performed using significantly larger pore size (i.e. >200 µm), which still are capable of retaining the medium, and provide stable humidity control options in a large enough volume for plant growth.

Figure 6:
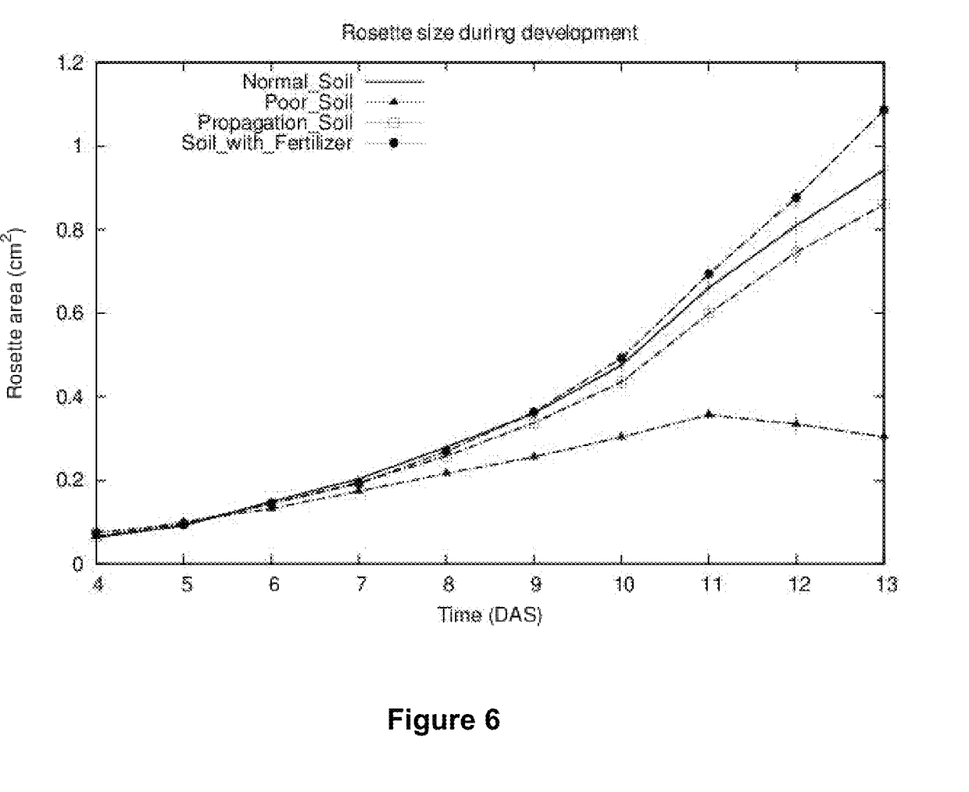
FIG. 6: *Arabidopsis* in vivo growth and soil type testing using the netwell assay.

Example 4. Soil Type Testing to Determine Differences in *Arabidopsis* Growth in the Netwell Assay Plants were grown as described in the above Netwell assay method. No treatment was added to the watering scheme, but a series of 4 plates, each with 24 *Arabidopsis* seedlings and each with a different type of soil granular housing medium were compared. The different soil types comprise soil with fertilizer, propagation soil, poor soil, and normal soil as a control (FIG. 6). Growth of individual plants was followed over time by daily imaging between 4-14 DAS. Projected rosette sizes were measured using image analysis procedures. Average rosette areas were calculated over time per soil type (FIG. 6). The soil containing plant fertilizer showed a plant growth enhancing effect as compared to the normal control soil, whereas the poor soil resulted in a significant reduced growth as compared to the normal control soil (FIG. 6), and finally the propagation soil and normal soil did not demonstrate significant differences in plant growth, as expected. Overall, the different soil types demonstrate also plate-to-plate robustness of the system to quantify between different plates.

Example 5. Different Concentration Treatments in Individual Wells of the Netwell Plate

*Arabidopsis* plants were grown as described in the above Netwell assay method. At 7 and 10 days after sowing (DAS), total duration of 16 days, 0.8 mL of treatment solution was added to each of the wells, with n=4 plants or wells per plate per treatment. Growth of individual plants was followed over time by daily imaging between 4-14 DAS. Projected rosette sizes were measured using image analysis procedures. Average rosette areas were calculated over time per treatment (FIGS. 7 and 8).

Figure 7:
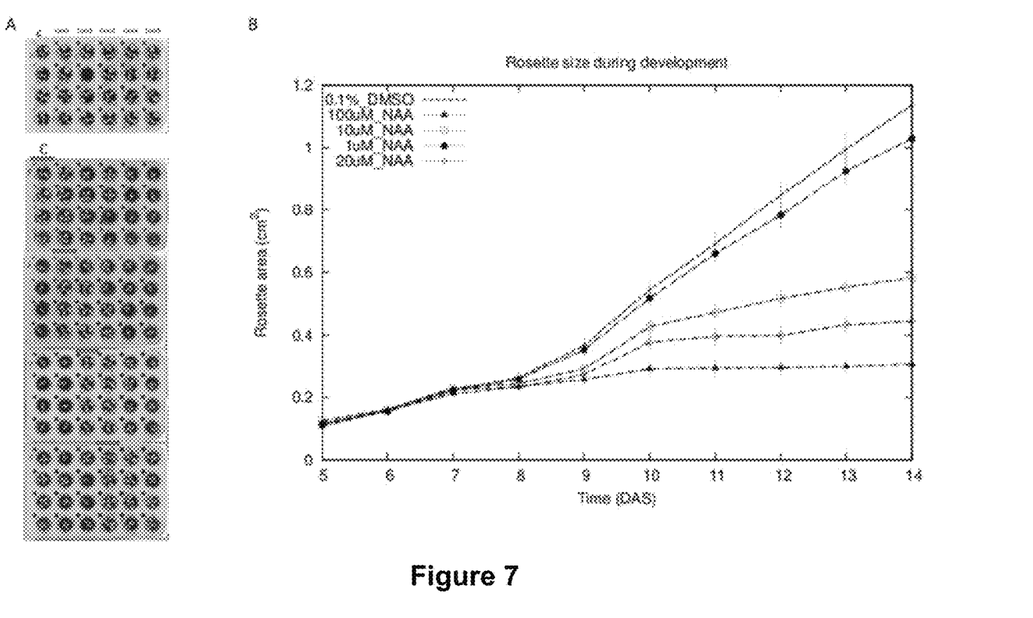
FIG. 7: *Arabidopsis* in vivo growth and different NAA concentration testing using the netwell assay.
Figure 8:
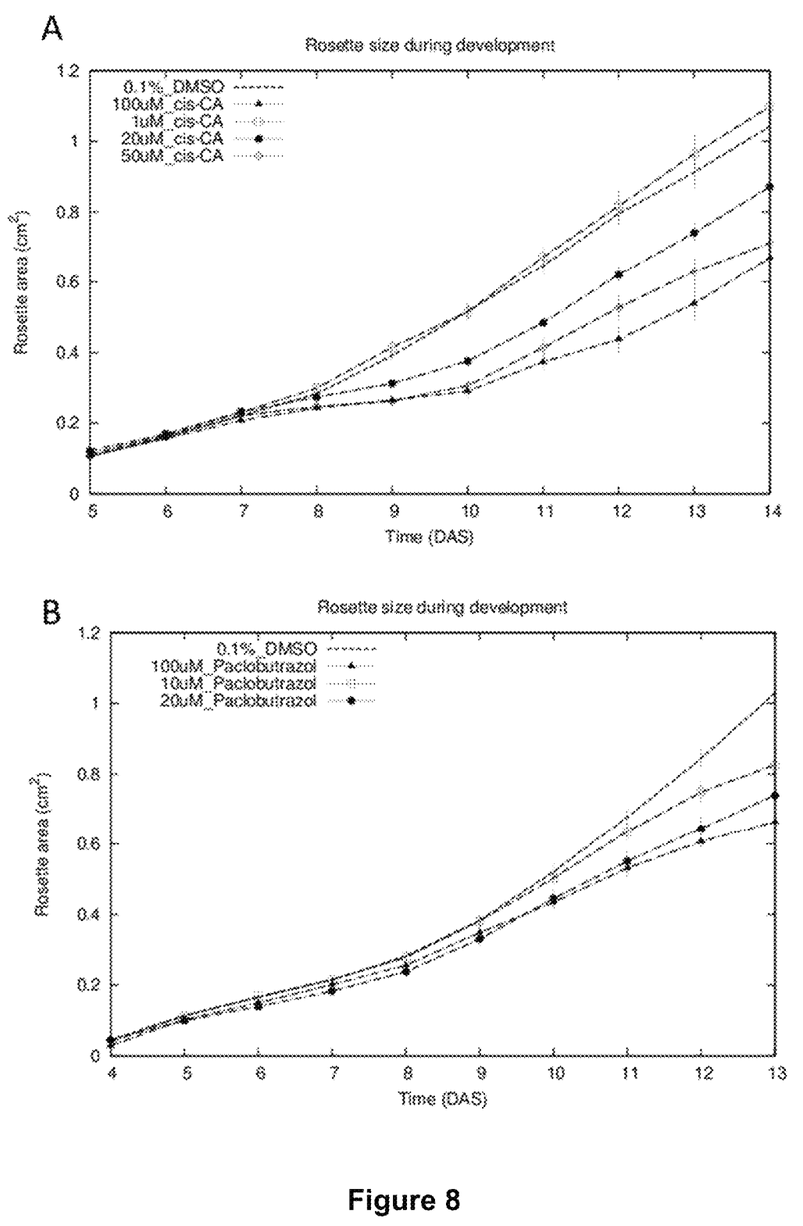
FIG. 8: *Arabidopsis* in vivo growth and compound testing using the netwell assay.

The treatment comprises a 1-Naphthaleneacetic acid (NAA) hormone treatment solution at different concentrations, as indicated in FIG. 7.

The wells from the plate were treated with a different concentration in each column. The experiments were repeated over 4 plates with a rotation of the concentrations per column to demonstrate the absence of a position effect (FIG. 7A; comprising of control samples in different columns). The average of all plates per concentration for each timepoint was calculated, and is shown in FIG. 7B for a concentration of 100 µM, 20 µM, 10 µM, and 1 µM, as compared to the negative control, which is DMSO (vehicle control). The higher the concentration of NAA during the treatment, the smaller the rosette size, as expected. Additionally, also 50 µM NAA treatment was included as the $5^{th}$ concentration, which resulted in a similar average Rosettes area per timepoint as compared to the highest 100 µM NAA concentration, indicating that a maximal inhibitory concentration was probably already reached at 50 µM NAA. This experiment also demonstrated that the intra-plate assay variation or position effect is nihil or very low.

Example 6. Compound Testing for Retarded *Arabidopsis* Growth in the Netwell Assay Plants were grown as described in the above Netwell assay method. At 7 and 10 days after sowing (DAS), total duration of 14 days, 0.8 mL of treatment solution, with n=4 plants or wells per plate per treatment. Growth of individual plants was followed over time by daily imaging between 4-14 DAS. Projected rosette sizes were measured using image analysis procedures. Average rosette areas were calculated over time per treatment (FIG. 8).

The treatment provided in FIG. 8A comprises an irrigation solution containing different concentrations of cis-cinnamic acid (cis-CA) and 0.1% DMSO as a control treatment. Treatment with the cis-CA-containing solution showed a slightly positive effect at 1 but at higher concentration, the compound becomes rather toxic for the plant and induces a plant growth retarding effect, with a dose response measured within the same plate for different concentrations at 20, 50, and 100 µM of cis-CA treatment versus the DMSO controls (FIG. 8A).

The treatment provided in FIG. 8B comprises an irrigation solution containing different concentrations of Paclobutrazol and 0.1% DMSO as a control treatment. Treatment with the Paclobutrazol-containing solution showed a plant growth retarding effect, with a dose response measured within the same plate for different concentrations at 10, 20, and 100 µM of Paclobutrazol treatment versus the DMSO controls (FIG. 8B).

The invention claimed is:
1. A multiwell plate system, the system comprising:
   an insert plate, and
   an irrigation plate for supporting the insert plate,
   wherein the insert plate is mounted on the irrigation plate,
      wherein the insert plate comprises a multiplicity of well openings in an insert plate body and a multiplicity of access holes in the insert plate body, wherein the access holes are equal in number to the well openings, and each of the access holes being positioned in the insert plate body adjacent to and separated from a corresponding well opening in the insert plate body, wherein a hollow chamber, defined by one or more walls, extends from each of the well openings, wherein the hollow chamber is closed at the end opposite the well opening by a porous membrane, wherein the porous membrane has a pore size of 200 μm to 1000 μm;

wherein an irrigation channel, defined by one or more walls, extends from each of the access holes and the irrigation channel is adjacent to and separated from a corresponding hollow chamber, wherein the irrigation channel ends in an opening opposite the access hole;

wherein the irrigation plate comprises a multiplicity of wells, each well corresponding in position to the hollow chambers of the mounted insert plate, wherein the wells are shaped to accept insertion of a corresponding hollow chamber as well as the irrigation channel adjacent to the hollow chamber thereby providing fluid communication between the irrigation channel and the hollow chamber via the irrigation plate well, and wherein the hollow chamber houses a granular medium and the porous membrane is configured to supply fluid from the irrigation channel to the granular medium via cappillary forces.

2. The multiwell plate system of claim 1, wherein the porous membrane is a hydrophilic mesh with a pore size of 400 μm to 600 μm.

3. The multiwell plate system claim 1, wherein the hollow chambers and access holes have a square, rectangular, rounded rectangular, oval rectangular, squircular, oval, or circular circumference.

4. The multiwell plate system of claim 1, wherein the insert plate and the irrigation plate have an identical square, rectangular, rounded rectangular, oval rectangular, squircular, oval or circular circumference.

5. The multiwell plate system of claim 1, wherein the irrigation plate contain 6, 12, or 24 wells.

6. The multiwell plate system of claim 1, wherein the insert plate is made from at least two different materials, a first material being a porous membrane, and a second material for the insert plate body.

7. The multiwell plate system according to of claim 6, wherein the porous membrane is made from hydrophilic mesh, and/or wherein second material is a non-transparent material.

8. The multiwell plate system of claim 6, wherein the second material is a temperature resistant material.

9. The multiwell plate system of claim 1, wherein said the granular medium is soil or comprises soil.

10. The multiwell plate system of claim 1, wherein the insert plate contains 6, 12, or 24 hollow chambers.

11. The multiwell plate system of claim 1, wherein the porous membrane is polystyrene.

12. An assay screening method for a compound, the method comprising:
introducing a sample into the granular medium of a multiwell plate system of claim 1;
adding an irrigation solution to the access hole;
treating the hollow chamber with a test-compound-containing solution via the access hole;
retaining a humidity level of the granular medium by replenishing with the irrigation solution; and
monitoring the sample in comparison to a control sample.

13. The method according to claim 12, wherein the sample is plant tissue, seedlings or seed.

14. The method according to claim 12, further comprising sealing exterior edges of the multiwell plate system.

15. The method according to claim 12, wherein treating the hollow chamber is performed robotically.

* * * * *